(12) United States Patent  (10) Patent No.: US 7,717,949 B2
Dorn  (45) Date of Patent: May 18, 2010

(54) LINING FOR BODILY LUMEN

(75) Inventor: Jurgen Dorn, Munich (DE)

(73) Assignee: C. R. Bard, Inc., Murray Hill, NJ (US)

( * ) Notice: Subject to any disclaimer, the term of this patent is extended or adjusted under 35 U.S.C. 154(b) by 257 days.

(21) Appl. No.: 10/572,191

(22) PCT Filed: Sep. 23, 2004

(86) PCT No.: PCT/EP2004/010691

§ 371 (c)(1),
(2), (4) Date: Apr. 11, 2006

(87) PCT Pub. No.: WO2005/030092

PCT Pub. Date: Apr. 7, 2005

(65) Prior Publication Data

US 2006/0259123 A1  Nov. 16, 2006

(30) Foreign Application Priority Data

Sep. 25, 2003 (GB) ................. 0322511.7

(51) Int. Cl.
A61F 2/06 (2006.01)
(52) U.S. Cl. .................................. 623/1.11
(58) Field of Classification Search ............... 623/1.11, 623/1.12; 29/517; 72/402
See application file for complete search history.

(56) References Cited

U.S. PATENT DOCUMENTS

| 4,576,534 A | 3/1986 | Barth et al. |
| 4,580,568 A | 4/1986 | Gianturco |
| 5,458,605 A | 10/1995 | Klemm |
| 5,569,296 A | 10/1996 | Marin et al. |
| 5,619,878 A | 4/1997 | Grosjean et al. |
| 5,697,948 A | 12/1997 | Marin et al. |

(Continued)

FOREIGN PATENT DOCUMENTS

DE  10016920  10/2001

(Continued)

OTHER PUBLICATIONS

USPTO Office Action Sep. 28, 2007.

(Continued)

*Primary Examiner*—Anhtuan T Nguyen
*Assistant Examiner*—Eric Blatt
(74) *Attorney, Agent, or Firm*—Rutan & Tucker, LLP

(57) ABSTRACT

A covered self-expanding stent (114, 130, 132) with a length of 200 mm or more can be restrained against axial movement with a pusher (40) within the lumen of the stent that carries a spiral of wire (48) that provides protrusions that are accommodated within a luminal covering layer (24) radially inside the stent body. The protrusions distribute the stress over the full length of the stent. The pusher can be removed from the stent lumen by "unscrewing" the spiral relative to the covering layer (24). When the stent expands, the pusher can be withdrawn proximally, out of the stent lumen, without any need for rotatory movement. The covered stent can utilize a variety of stenting rings (110-118) along its length that manifest different mechanical properties so that the implant can exhibit mechanical properties that vary over its length, to suit the specific body and stenting site to which it is to be introduced.

4 Claims, 3 Drawing Sheets

U.S. PATENT DOCUMENTS

| | | |
|---|---|---|
| 5,749,880 A | 5/1998 | Banas et al. |
| 5,776,141 A | 7/1998 | Klein et al. |
| 5,876,448 A | 3/1999 | Thompson et al. |
| 5,920,975 A | 7/1999 | Morales |
| 5,928,258 A | 7/1999 | Khan et al. |
| 6,063,092 A | 5/2000 | Shin |
| 6,113,628 A * | 9/2000 | Borghi ............ 623/1.16 |
| 6,143,014 A | 11/2000 | Dehdashtian et al. |
| 6,203,568 B1 | 3/2001 | Lombardi et al. |
| 6,210,429 B1 * | 4/2001 | Vardi et al. ............ 623/1.11 |
| 6,214,039 B1 | 4/2001 | Banas et al. |
| 6,451,047 B2 | 9/2002 | McCrea et al. |
| 6,471,718 B1 | 10/2002 | Staehle et al. |
| 6,607,551 B1 | 8/2003 | Sullivan et al. |
| 6,613,075 B1 | 9/2003 | Healy et al. |
| 6,758,858 B2 | 7/2004 | McCrea et al. |
| 6,776,791 B1 | 8/2004 | Stallings et al. |
| 6,796,998 B2 | 9/2004 | Schaldach et al. |
| 6,858,034 B1 | 2/2005 | Hijkema et al. |
| 6,945,989 B1 | 9/2005 | Belelia et al. |
| 7,011,675 B2 | 3/2006 | Hemerick et al. |
| 2001/0032009 A1 | 10/2001 | Layne et al. |
| 2001/0039446 A1 | 11/2001 | Edwin et al. |
| 2002/0029076 A1 | 3/2002 | Yee |
| 2002/0038143 A1 | 3/2002 | McCrea et al. |
| 2002/0058993 A1 | 5/2002 | Landau et al. |
| 2002/0138966 A1 | 10/2002 | Motsenbocker |
| 2002/0147490 A1 | 10/2002 | Pletzer et al. |
| 2002/0156516 A1 | 10/2002 | Vardi et al. |
| 2002/0193863 A1 | 12/2002 | Rourke et al. |
| 2003/0032999 A1 | 2/2003 | Huang |
| 2003/0153969 A1 | 8/2003 | Dehdashtian et al. |
| 2004/0106977 A1 | 6/2004 | Sullivan et al. |
| 2004/0204749 A1 | 10/2004 | Gunderson |
| 2006/0184225 A1 | 8/2006 | Pryor |
| 2006/0184226 A1 | 8/2006 | Austin |
| 2006/0216404 A1 | 9/2006 | Seyler et al. |
| 2007/0156251 A1 | 7/2007 | Karmon |

FOREIGN PATENT DOCUMENTS

| | | |
|---|---|---|
| DE | 10212707 | 10/2003 |
| DE | 20306823 U | 11/2003 |
| EP | 0596145 | 5/1994 |
| EP | 0873731 | 4/2000 |
| EP | 0788332 | 11/2000 |
| EP | 0836447 | 12/2002 |
| EP | 0826346 | 6/2003 |
| FR | 2742042 | 6/1997 |
| FR | 2760351 | 9/1998 |
| JP | 2003500103 | 1/2003 |
| WO | WO96/28115 | 9/1996 |
| WO | WO 98/31305 | 7/1998 |
| WO | WO99/55255 | 11/1999 |
| WO | WO 01/05331 | 1/2001 |
| WO | WO01/21103 | 3/2001 |
| WO | WO01/34061 | 5/2001 |
| WO | WO02/15820 | 2/2002 |
| WO | WO03/003944 | 1/2003 |
| WO | WO03/049641 | 6/2003 |
| WO | WO2004/062458 | 7/2004 |
| WO | WO2004/096091 | 11/2004 |

OTHER PUBLICATIONS

USPTO Office Action for U.S. Appl. No. 10/552,886 dated Apr. 2, 2008.

Aug. 6, 2009 Japanese Examination Report (translated) in Japanese application No. 2006-527350.

* cited by examiner

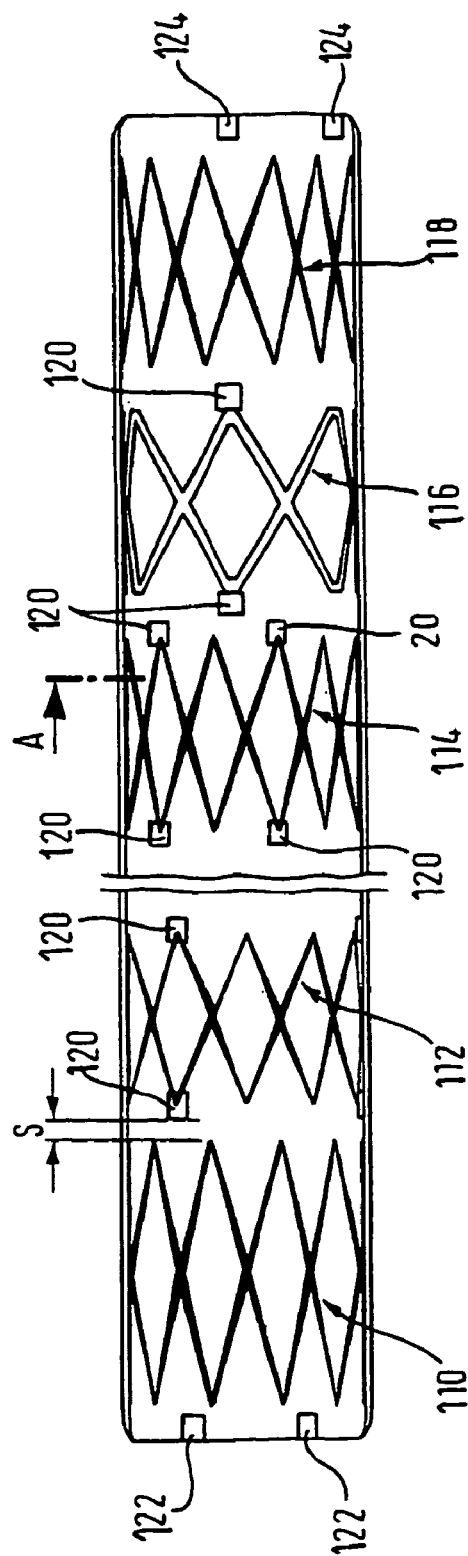

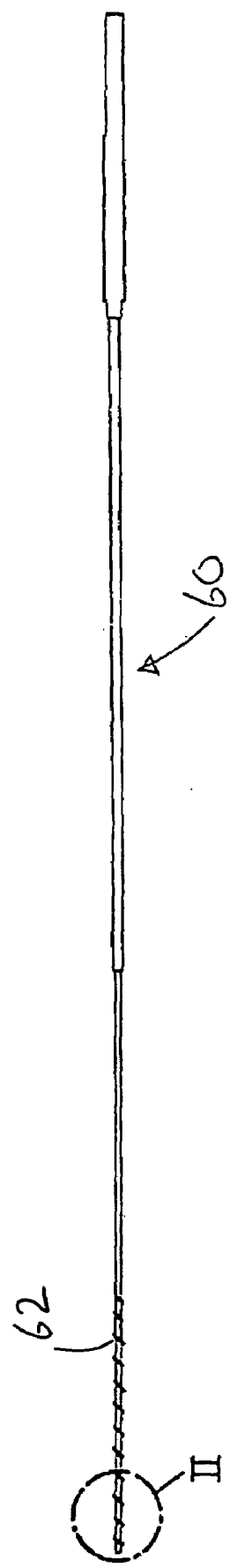
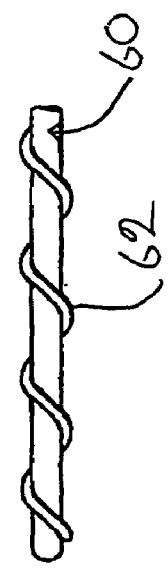
Fig.3
Fig.4

LINING FOR BODILY LUMEN

PRIORITY

This application is a national stage application under 35 USC §371 of International Application No. PCT/EP2004/10691, filed Sep. 23, 2004, claiming priority to United Kingdom Application No. GB 0322511.7, filed Sep. 25, 2003, each of which is incorporated by reference into this application as if fully set forth herein.

BACKGROUND

This invention relates to a self-expanding stent graft for percutaneous transluminal delivery. Such a prosthesis can be regarded as a "lining" for a short length of a bodily lumen. Such lumens are often arteries but need not be. For example, stents are often used in the ureter or in the biliary tree. A prosthesis of larger diameter could be placed in the oesophagus or the trachea.

Up until now, these prostheses have had a relatively short length, and are used for treating short lengths of bodily lumen, where disease is local. The present inventor has realised that it would be useful to have a prosthesis with a length significantly longer than that available with the current stents and grafts. Specifically, the present inventor has recognised the usefulness of a stent graft having a length of at least 200 mm, and has realised how this objective can be accomplished.

In the early days of development of percutaneous, catheter-delivered stents for bodily lumens, there were proposed stainless steel cages to be mounted on a balloon and expanded at the site of stenting by inflation of the balloon in the stent lumen, to cause plastic deformation of the struts of the stainless steel cage, to achieve one way expansion of the radius of the cage, whereupon deflation of the balloon would allow the delivery system to be removed, leaving the expanded stent cage in place. Thereafter, it was proposed to cover the stainless steel cage stenting rings, to make available corresponding stent grafts.

Another form of stent, also of stainless steel, was the self-expanding form of stent, contained within a sheath until proximal withdrawal of the sheath would allow the resilient stenting ring to expand radially by elastic deformation, again allowing the delivery system thereafter to be withdrawn proximally.

The number of materials that are biologically compatible, yet with mechanical characteristics strong enough for stenting, is severely limited. Besides stainless steel, another available material is a nickel-titanium shape memory alloy which goes under the trade mark NITINOL. Stents of this material are self-expanders, again confined by a radially-overlying sheath which is withdrawn proximally to release the stent to expand radially. Another candidate is a cobalt-chromium-nickel alloy identified by the trademark PHYNOX.

It will be appreciated that proximal withdrawal of a surrounding sheath of a self-expanding stent requires a tension force in the sheath which, other things being equal, increases as the axial length of the stent increases, since the entire length of the stent within the sheath is, at the site of stenting, imposing radially outward pressure on the sheath, thereby raising the forces of friction acting between the stent and the sheath. Similarly, for the operation of loading the self-expanding stent into a suitable catheter-based delivery system, some means has to be found for advancing the sheath over the length of the stent, or pulling the stent into the sheath, until its full length is within the sheath.

The forces of friction have, until now, imposed an upper limit on the overall dimensions of length and diameter of a self-expanding stent graft that can feasibly be installed in a surrounding sheath, and then released from the sheath at the site of stenting.

The present inventor has found a way to install and deliver self-expanding stent grafts of greater dimensions than hitherto, in particular, stent grafts of greater length than hitherto.

International Patent Application No. PCT/EP2004/004486 (PCT 486), published as WO 2004/096091, is from the present inventor and declares the priority of British Patent Application No. 0309616.1 of the present inventor. The present specification includes disclosure from the description, claims and drawings of PCT/EP2004/004486.

From consideration of PCT 486, it is immediately apparent that a feature useful for loading and delivery of extra long self-expanding stent grafts, covered stents and other implants is an element that sits within the lumen of the stent graft and is characterised by a spiral formation on its radially outward-facing cylindrical surface. Edge surfaces which define the spiral form engage with the luminal face of the graft or cover material of the implant, throughout the length of the implant. In this way, axial force can be passed between the implant and the element within its lumen, along the full length of the implant, via the spiral form edges. It is this distribution of axial forces along the full length of the implant which carries, along the full length, the friction forces operating between the abluminal surface of the implant and any surrounding sheath of a delivery system for the implant.

With the use of such a means to distribute friction forces along the full length of the implant, it is envisaged that implants of significantly more than 200 mm length could be deployed. Specifically, it is envisaged to deploy, with the spiral form element mentioned above and shown in the annex to the specification, stent grafts of around 500 mm in length. Thus, for the first time, it becomes feasible to contemplate a stent graft lining for, for example, the femoral-popliteal artery of the human leg, along a substantial or even major part of its length.

DE-A-10016920 discloses electroplating a metal mesh workpiece with a length of 5 to 200 mm prior to using the workpiece to make medical implants.

FR-A-2760351 discloses making from filament a helical pattern stent which may have a length more than 20 mm, or even more than 50 mm.

FR-A-2742042 discloses making a vascular prosthesis to replace natural bodily tissue and with a length which may be as much as 120 cm.

WO 03/049641 discloses a radially expandable stent which consists of a plurality of axially spaced radially expandable cylindrical stenting rings aligned along a common axis to define a lumen and arranged around a polymer tube. The tube provides longitudinal and flexural flexibility to facilitate transluminal advance and delivery through a tortuous bodily lumen, and the rings provide the strength to maintain patency of the lumen EP-A-788 332 discloses a self-expanding braided metallic stent tube and a delivery system that includes a soft annulus within the stent lumen that deforms and mechanically engages with the mesh of the stent for restraining the stent from axial movement relative to the inner catheter of the delivery system, during axial movement of a sleeve surrounding the stent. The disclosure of EP-A-596 145 is similar.

EP-A-836 447 discloses a system for delivering a self-expanding stent, in which a stopper ring on an inner catheter abuts the proximal end of the stent tube during proximal withdrawal of a sheath which surrounds the stent.

The tubular envelope of a stent usually has apertures through its wall thickness to permit radial expansion. Thus, an uncovered or "bare" stent has a tube wall that is normally liquid-permeable. However, there are many occasions when a stent with a liquid-impermeable wall that is not apertured would be desirable. To meet these needs, a family of "covered" stents have been developed. Applicant has particular experience with stent tubes provided with a covering of expanded polytetrafluoroethylene (ePTFE). Typically, the stent tube is covered by luminal and abluminal covering layers of ePTFE, which are bonded to each other through the apertures in the stent tube wall.

During manufacture of stents and delivery systems, attention must be paid to sterility. Specifically, one needs procedures for loading a covered stent into a catheter delivery system that will allow sterile conditions to be maintained, or at least thereafter achieved.

Typically, to introduce a covered self-expanding stent into a catheter delivery system, a tool needs to be provided that compresses the covered stent radially inwardly, down to a diameter which is smaller than the available diameter of the lumen of the delivery system that is to receive the compressed covered stent. Clearly, any structure within the lumen of the stent that resists further inward compression is better avoided, when the objective is to compress the stent radially inwardly as much as the system will tolerate, so as to keep the outside diameter of the delivery system at its distal tip as small as possible.

However, the stent has to be maintained at the stenting site during proximal withdrawal of the surrounding sheath, for progressive release of the stent at the stenting site. If there is no structure within the lumen of the stent, then the entire stress imposed on the stent, to prevent it moving proximally with the proximally withdrawing surrounding sheath, has to be carried on the proximal end annulus of the compressed stent. Often this is not really a problem, especially when the stent is short and not particularly highly compressed radially inwardly, and especially when friction between the compressed stent and the surrounding sheath can be brought to a particularly low value.

Nevertheless, it is important for management of fatigue resistance to avoid imposing on any point of the stent tube a level of stress that is higher than the designed maximum. A stent tube made of metal is susceptible to fatigue failure, if only because it is subject to cyclic stress at the frequency of the heartbeat of the body in which it is installed. For this reason, regulatory authorities require stringent fatigue performance standards which impose on manufacturers of stents and delivery systems an onerous burden to avoid any unforeseen stresses on the stent tube.

The state of the art contains numerous suggestions to use an element within the lumen of the stent to restrain the stent from proximal withdrawal when the surrounding sleeve is withdrawn proximally. However, these systems are of interest only for bare stents, because they rely upon mechanical interaction between surfaces on the stent pusher within the stent lumen, and boundary surfaces of apertures within the wall thickness of the stent tube.

The present disclosure explains how to load self-expanding covered stents into catheter delivery systems which offers better management of stress within the stent tube, facilitates quality control and maintenance of sterile conditions, and is applicable to a range of stent tube designs. In a nutshell, a pusher is provided within the lumen of the covered stent, which exhibits protrusions along the length of the lumen, that interact with the covering of the stent along the length of the stent.

By distributing over the full length of the stent tube lumen the forces which necessarily have to be imposed on the stent in order to:

1. load it into a delivery sheath; and/or
2. restrain it from proximal movement during proximal withdrawal of the delivery sheath during placement of the stent at the stenting site one can manage the distribution of stress within the stent tube so that it is distributed more or less homogeneously, rather than concentrated at one end of the stent tube. By using the covering of the stent as a link in the chain of stress distribution from the pusher to the sheath, one can further avoid any point at all within the metal stent tube which is subject to stress at a level higher than a prescribed design maximum. By their nature, stent coverings are more flexible than the stent tube itself, so have the capability to distribute stress from a point on a metallic stent pusher to an area, or volume, of the material of the stent tube.

Furthermore, the flexibility of the stent covering is sufficient to accommodate the protrusions of the pusher, irrespective where they lie in relation to the apertures of the stent lumen. With the present concept, there is no need to align in any way the protrusions of the stent pusher with the apertures of the stent lumen. Thus, a further technical effect is valuable simplicity and speed of operation in loading a range of different covered stent products into their corresponding delivery systems.

Yet a further advantage is that the stent pusher needs no undercut or rebated surfaces to achieve its effect, and the pusher has an outside diameter which is smaller than the inside or luminal diameter of the stent tube. These factors give greater reassurance that, when the stent has been placed, and the pusher has to be withdrawn from the stent lumen, there will be no inadvertent or unintended snagging of surfaces of the pusher on surfaces of the covered stent, or indeed of any bodily tissue that might impinge on the surfaces of the stent pusher after it has been withdrawn proximally out of the stent lumen.

Of particular interest is a stent pusher with protrusions arranged helically. Such protrusions will achieve the desired pushing effect when the pusher is subject to axial stress. However, arranging the protrusions helically would allow the pusher to be withdrawn from the stent lumen, even while the stent is within the sheath of the delivery system, simply by "unscrewing" the shaft of the pusher until the helical protrusions emerge, by continued rotation of the pusher relative to the stent, out of the lumen of the stent. In this way, one can employ the stent pusher as part of a system for loading a covered stent into a sheath, but then remove the pusher, and pass the sheath stent assembly onwards for incorporation into a delivery system which will use an entirely different stent pusher.

To assist understanding of the present invention, to be described below, and to assist in its realisation, reference will now be made to FIGS. 3 to 5 of the accompanying drawings (which come from above-mentioned PCT 486) and in which:

FIG. 3 is a side view of a tool for loading a covered self-expanding stent into a sheath;

FIG. 4 is an enlarged view of the distal end (II) of the tool of FIG. 3; and

FIG. 5 is an axial diametral section through the distal tip of a stent delivery system.

FIG. 5 shows only the distal tip of the delivery system, but the remainder of the system is not part of the contribution which the present invention makes to the art and, in any event, is familiar to those skilled in this art. The basic components of a conventional delivery system for a self-expanding stent are an inner catheter and an outer sheath, the purpose of the outer sheath being to confine the self-expanding stent radially, to the small radius delivery configuration, until its release at the site of stenting. The purpose of the inner catheter is to restrain the stent from proximal movement with the sheath, while the sheath is being withdrawn proximally.

Looking at FIG. 5 of the drawings, the outer sheath 10 of the delivery system has an integral tapered tip 12 which narrows down to an end ring 14 of a diameter appropriate to receive a guidewire (not shown). Confined within the sheath is a covered stent of which the structural foundation is a stent body 20 which is an apertured tube of nickel-titanium shape memory alloy. The stent is covered by an outer layer 22 of ePTFE on the abluminal surface of the stent body, and a covering layer 24 of ePTFE on the luminal inner surface of the stent body 20, with the inner and outer layers 24 and 22 being fused together where they can be pressed together within the apertures 26 of the stent body.

Between the luminal and abluminal surfaces of the stent body 20 is a wall thickness of the metallic stent material annulus. This annulus lies between the luminal and abluminal major surfaces of the stent body and, in the specification, we use the terminology "envelope" to indicate the generalised surfaces of the luminal and abluminal major wall surfaces of the stent body. Thus, the outer layer 22 lies outside the abluminal envelope stent body 20, except where it protrudes into the apertures 26 for fusing with the inner layer and, likewise, the inner layer 24 lies radially within the luminal envelope of the stent body 20 except where it protrudes radially outwardly into the stent body apertures 26.

The stent body carries a ring of tantalum radiopaque markers 28 at its distal end and a second ring of radiopaque tantalum markers 30 at its proximal end. It will be appreciated that the presence of these markers may further militate against pushing structures that bear against the end surface of the stent to be deployed.

The inner catheter 40 defines a guidewire lumen 42. Conveniently, the inner catheter 40 is based on a stainless steel hypo tube. This of course endows the entire delivery system with substantial pushability, but the hypo tube can also be made remarkably flexible for the desired trackability of the system through particularly tortuous bodily lumens. In any event, if stainless steel is not flexible enough for the distal zone of the delivery system, then it would be feasible to build the inner catheter 40 from other more flexible materials such as particular polymers.

The stent delivery system can be arranged as an over-the-wire system with a full length guidewire lumen, or a rapid exchange system with a guidewire lumen only in a distal zone of the system. The outer sheath 10 can be withdrawn by a full length outer catheter or a pull wire within a shaft lumen. For an example of delivery systems of the present Applicant, see WO 03/003944 and WO 2004/062458.

The inner catheter has an abluminal surface 44 which carries on it a wire 46 arranged as a helix so as to provide a plurality of protrusions (at least when seen in section as in the drawing) on the abluminal surface 44. In the illustrated embodiment, the wire is of stainless steel, fixed to the stainless steel tube 40 by deposits 50 of a bonding material which could be a weld bead or a suitable adhesive.

In any event, as can be seen on the drawing, when the stent body is radially inwardly compressed down onto the inner catheter 40, the inner ePTFE layer 24 deforms to accommodate the protrusions 48, but the protrusions 48 do not reach radially outwardly as far as the luminal envelope of the stent body 20.

In use, when the illustrated distal tip zone has been brought to the site of stenting, the outer catheter 12 is carefully and progressively withdrawn proximally so that the tip stretches and slides over the outer ePTFE layer 22 of the stent, progressively releasing the stent, starting at its distal end near the markers 28.

As the stent progressively expands, the inner ePTFE layer 24 moves radially outwardly away from the protrusions 48 until, with complete withdrawal of the tip 12 proximally beyond the proximal ring of radiopaque markers 30, the stent is fully released. It will be appreciated that there is then a substantial annular gap between the lumen of the expanded stent and the envelope containing the protrusions 48, enabling the inner catheter 40 also to be withdrawn proximally from the lumen of the stent without any snagging of the inner catheter 40 on any part of the stent.

It will be appreciated that, for loading a stent into a sheath, an analogous sequence of steps may be performed, with radially inward compression of the stent body down onto the protrusions 48 of a loading tool which has a shape in section analogous to that of the inner catheter 40. Once the stent has been so compressed, a suitable sheath can be offered up to one end of the compressed stent tube, and then the stent can be urged axially into the sheath by imposing an axial force on the line of protrusions 48 through the tube 40 on which they amounted, so that this force is transferred from the protrusions 48 to the inner layer 24 and thence to the stent body 20 and the outer layer 22, so that the entire covered stent device is urged by the protrusions 48 into the receiving sheath.

A particular advantage of the helical structure of protrusions 48 as shown in the drawing is that the pusher within the stent lumen can be removed trouble-free from the lumen of the stent even when it is in a compressed configuration within a sheath as shown in the drawing, simply by "unscrewing" the pusher from within the stent lumen.

Drawing FIGS. 3 and 4 show a suitable loading tool 60, long enough to push the covered stent along the full length of the outer catheter 10, after being compressed and introduced and advanced into the proximal end of the outer catheter. The tool 60 features at its distal end a radially-outwardly protruding wire spiral 62 with a configuration corresponding to that of the protrusions 48 and the inner catheter 40 (although non-corresponding configurations are also feasible). The covered stent is compressed around the protrusions 62 before the tool 60 is used to urge the covered stent by means of the protrusions 62, from the proximal to the distal end of the outer catheter.

The illustrated embodiment shows a system in which the tapered distal tip of the stent delivery system is carried on the distal end of the outer catheter. Those skilled in the art are well-aware that many proposed delivery systems feature a tapered tip on the inner catheter instead. The present invention is just as useful in such systems as it is in systems, as illustrated, with the tapered tip on the outer catheter.

The stent on which the present device operates can be an covered self-expanding stent. The stent which is the basis of the illustrated embodiment is the one that is the preferred embodiment of WO 2002/015820 which is cut from a nickel-titanium tube. However, the invention is equally applicable to other stent design philosophies, such as stents fabricated from wire (one example is the Gianturco "Z" stent made from zig zag wire rings) or other metals, such as stainless steel. The invention is particular useful for covered stents in which only the cover connects adjacent ones of a plurality of stenting rings, because the engagement of the pusher over the full length of the stent should avoid any tendency for the stent covering to "concertina" between the stenting rings when pushed only from its trailing (usually proximal) end.

SUMMARY OF THE INVENTION

In accordance with one aspect of the present invention, there is provided a self-expanding stent graft for percutaneous transluminal delivery, characterised by a length of 200 mm or more. According to another aspect of the invention, there is provided a percutaneous transluminal implant delivery system carrying a stent graft having a length of at least 200 mm. Yet another aspect of the present invention provides a method of loading and unloading a covered stent with a length of 200 mm or more into and out of a percutaneous transluminal stent delivery system.

Advantageously, the stent graft comprises a plurality of self-expanding metallic stent rings, axially spaced from one another, yet connected through luminal and abluminal layers of graft material bonded to each other to sandwich the stenting rings between the layers. The graft material should be of biologically compatible material, such as polytetrafluoroethylene, whether PTFE or ePTFE. Likewise, the stenting rings should be of a biologically compatible material and this could be, for example, stainless steel or Nitinol.

The stent rings can be all the same, all different from one another, or some the same and some different. Thus, for example, different rings could have different ability to expand radially outwardly against different amounts of radially inward pressure from lumen wall bodily tissue.

It will usually be advantageous to provide at least one of the stenting rings with at least one radiopaque marker. The electrochemical potential of tantalum is similar to that of Nitinol, whereby a tantalum marker in electrical contact with a Nitinol stenting ring can be tolerated, without electrochemical corrosion presenting a problem. Nevertheless, this does not exclude the use of other metals, such as gold, as radiopaque markers.

It is rare for a bodily lumen to be devoid of side branches or collateral lumens over anything more than a short length of the lumen. Thus, one consequence of lining a bodily lumen over a substantial length is that collateral channels will be blanked off by the graft material. Within the scope of the present invention it is contemplated to provide through-passages in the graft material, whereby a collateral channel may be placed in fluid communication with the lumen of the stent graft. Of course, when deploying the stent graft, a means must be found for aligning the pre-formed through-passage with the desired collateral channel, but this can be accomplished by placing radiopaque markers on the stenting rings axially either side of the through-passage so that they are spaced peripherally around the through-passage. Then, with the collateral channel identified by the radiologist, placement of the radiopaque markers in line with the identified collateral channel should put the through-passage of the stent graft material in line with the selected collateral channel, to achieve the desired fluid communication.

Clearly, mapping the bodily lumen to be stented enables the custom building of a stent graft, with selection of particular stenting rings of desired dimensions and stenting strength arranged along the full length of the stent graft in accordance with the map, and selected stenting rings carrying radiopaque markers placed in predetermined locations along the length of the stent graft, and around its circumference, for alignment of through-passages in the cylindrical wall of the stent graft and bodily side lumens collateral with the main lumen to be stented.

Some bodily lumens to be stented are notably tortuous. Others are not so tortuous, but are nevertheless accessible by catheter only through tortuous approach lumens. There is accordingly very often the need for any stent graft to be capable of being advanced through tight bends. Clearly, the closer individual stent rings are placed, one next to the other, along the length of the stent graft, the greater will be the difficulty for the stent graft to negotiate a tight bend, as adjacent stenting rings moving through the bend butt up against each other on the inside of the bend.

Accordingly, in another aspect of the present invention, there is provided a stent graft which comprises a plurality of stenting rings sandwiched between luminal and abluminal layers of graft material, the stenting rings exhibiting a plurality of terminal apices around the circumference, said apices defining a maximum extent of the respective stenting ring in an axial direction, and wherein two axial adjacent said rings are sandwiched within the graft material layers in orientations relative to each other rotationally about the long axis of the stent lumen such that each apex of one said ring lies circumferentially between two adjacent apices of the facing ring of terminal apices of said next adjacent stenting ring whereby, when the stent graft bends in a tortuous lumen, an apex approaching the ring of terminal apices of the next adjacent stenting ring may advance into the ring between said two adjacent apices, thereby permitting a greater degree of stent bending between two closely adjacent stenting rings than would be the case when each terminal apex is axially aligned with a facing terminal apex on the next adjacent stenting ring.

It will be appreciated that the alternative option, of spacing the stenting rings further apart from each other axially along the length of the stent graft, is disadvantageous when all the available strength of the stenting rings is needed to press on the tissue defining the walls of the bodily lumen to be stented. The longer the gaps along the axis of the stent graft, between adjacent stenting rings, the more work each stenting ring has to do to urge the bodily tissue radially outwards and keep the lumen patent.

A not insignificant aspect of the present invention is that electrical insulation of axially adjacent stenting rings, with each insulated stenting ring having a relatively short axial length, improves the opportunities for magnetic resonance imaging (MRI) visualisation of the content of the lumen of the stent graft. This is in contrast with the behaviour of a "classic" cylindrical stent cage matrix, which performs during MRI imaging like a Faraday cage to interfere with visualisation of the material within the stent lumen.

Thus, it will be appreciated that a stent graft in accordance with the present invention can provide a lining over an extended length of a bodily lumen, with a configuration and set of mechanical properties which is custom-built to meet the "specification" of the bodily lumen to be stented, which specification can be drawn up by "mapping" the lumen in question, prior to construction of the stent graft. Then, the custom-made stent graft can be installed, using radiological techniques to align through-passages in its cylindrical wall with collateral channels to the bodily lumen being stented. Then, performance of the stent graft can be monitored using MRI procedures, notwithstanding the presence of complete rings of metal, because the axial extent of each metal ring can be kept small, with adjacent rings being insulated from each other.

This is not to exclude the possibility that the stenting rings of stent grafts in accordance with the present invention can be constructed with conductivity breaks arranged around the circumference of each stenting ring, further to frustrate the generation of eddy currents within the metal structures, and thereby further ameliorate any adverse effect on MRI imaging of the presence of metal within the field of view.

Indeed, it is a characteristic of the present invention that its stent grafts can accommodate present best practice in graft materials and present best practice in stenting devices. For example, there is currently much activity with stenting devices to find constructions that interfere less with MRI techniques, and there is intense activity to use graft materials to carry biologically active materials, such as drugs, on the surface of the graft material, or within its bulk. All of these techniques should be available for use with stent grafts in accordance with the present invention.

BRIEF DESCRIPTION OF THE DRAWINGS

For a better understanding of the present invention and to show more clearly how the same may be carried into effect, reference will now be made, by way of example, to the accompanying drawings, in which:

FIG. 1 is a side view of both ends (broken away) intermediate the ends of a stent graft in accordance with the present invention;

FIG. 2 is a transverse section, on the line A of a small part of the circumference of the stent graft of FIG. 1; and FIGS. 3 to 5 as have already been introduced and described earlier in the is specification.

DETAILED DESCRIPTION OF THE PREFERRED EMBODIMENTS

Figure 5:
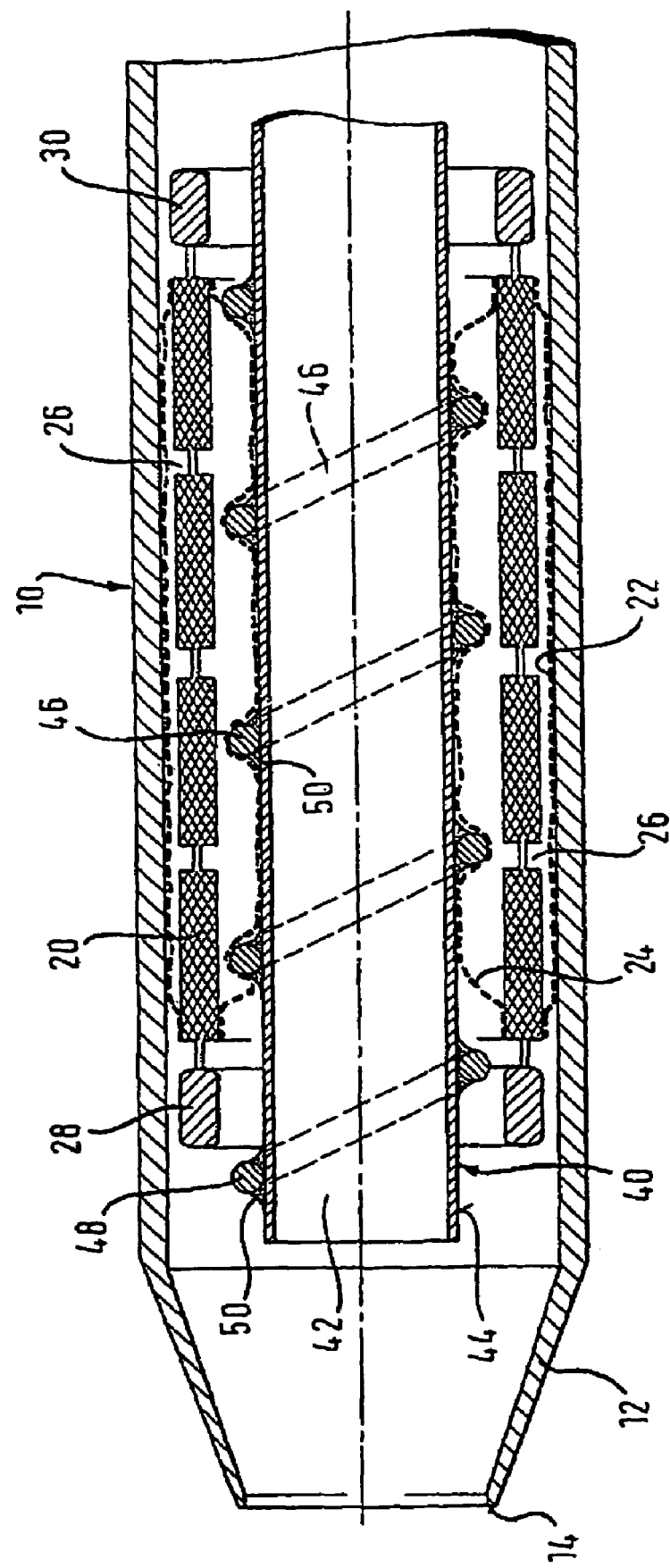

In FIG. 1, there can be seen a schematic representation of a stent graft, in longitudinal view, depicting five discrete and axially spaced stenting rings 110, 112, 114, 116 and 118. It should be understood that the length of the stent graft is far greater than is shown in FIG. 1, the length being broken away at S between rings 110 and 112, with any number of additional rings located between rings 110 and 112, to make up a stent graft very much longer, in relation to its diameter, than what is shown in FIG. 1. However, FIG. 1 puts across an important aspect of the present invention, that the stenting rings of the device are discrete, and so can be different from each other, as indeed are the rings depicted in FIG. 1.

Normally, the stenting rings will be of the same material, and of the same pattern and configuration of cell, if only for performance, planning, management and prediction, but this is not to exclude embodiments in which different stenting rings are made of different materials. Even with the same material, and the same basic cell pattern and configuration, changes of strut length and strut cross-section can change substantially the stenting "power" of each ring of the device, and this power can be modulated to fit the requirements of the bodily lumen in which the stent graft is to be placed.

Individual stenting rings can carry individual radiopaque marker elements. The state of the art contains many proposals for providing such markers. However, the present inventor prefers at the moment the radiopaque marker technology found within LUMINEXX stents of the present applicant, and which are described in the corresponding patent application, published as WO 02/015820, within which the radiopaque markers are designated as "spoons" because they have a curvature within the circumference of the stenting ring in which they are placed. Such radiopaque markers are designated in FIG. 1 with reference 120.

As best seen in FIG. 2, the struts of the stenting rings are encapsulated within a luminal layer 130 and an abluminal layer 132 of expanded polytetrafluoroethylene, each such layer having an overall cylindrical shape and extending from one end of the stent graft to the other, thereby connecting in an electrically non-insulating manner, all of the axially spaced stenting rings of the device. The technology for building a stent graft with stenting rings placed between luminal and abluminal cylindrical components of ePTFE is described in patent publications of IMPRA a sister company of the present applicant, including WO 96/28115.

Any patent publication mentioned in this specification is incorporated by this reference, at least to the extent that it assists readers to put the present invention into effect.

As explained in the IMPRA patent publications, it is convenient to lay-up the components of the stent graft with the ePTFE luminal and abluminal layers not yet fully sintered. With the components of the device correctly placed relative to each other, heat and pressure is applied, to bring the abluminal and luminal PTFE layers 132 and 130 into intimate contact between the struts of the stenting rings (strut 114 is shown in FIG. 2), and then sintering the ePTFE so that the luminal and abluminal layers are sintered together in this process step, thereby locking the struts of the stenting rings in position relative to the surrounding ePTFE material and, in turn, relative to the struts of the other stenting rings within the device.

Furthermore, such sintering together of the luminal and abluminal layers 130 and 132 can be used to encapsulate further radiopaque markers wherever they are required within the length of the stent graft. For example, shown in FIG. 1 is a plurality of radiopaque markers, which might be of gold or platinum or tantalum, at one end of the stent graft, to define that end radiologically, and a further set 124 of further radiopaque markers, at the other end of the stent graft.

It is of the essence of the present invention to contribute to the state of the art how to realise, and deploy, a stent graft substantially longer than the stent grafts that have hitherto been proposed. One way to accomplish this step, as envisaged by the present inventor, lies in adopting the technology which has been called ALFER and which is described above, in drawing FIGS. 3 to 5 and in above-mentioned PCT/EP2004/004486.

It will be appreciated that the step of loading an extra long stent graft, such as is shown in FIG. 1, into a surrounding sleeve of a delivery device can be accomplished stepwise by placing a spiral form ALFER mandrel within the lumen of the stent graft and then advancing the lumen into a crimping device which squeezes selected stenting rings radially inwardly, to bring the diameter of the stent graft, within the crimping device, to a diameter small enough to be advanced into the lumen of the surrounding sleeve of the stent graft delivery system. For examples of disclosures of crimping devices, see WO 01/21103, US 2002/0138966 A1, DE 10212707 A1 and DE-U-20306823.8. For other proposals, see the belt devices of WO 99/55255, EP-A-826346 and EP-A-873731.

Whereas stainless steel stenting rings are resilient and springy even at low temperatures, it is a distinctive feature of nickel-titanium shape memory alloy stenting rings that, when they are cooled down to sub-ambient temperatures, they remain in the crimped squeezed low diameter configuration, and do not exhibit the springiness and resilience that they exhibit at body temperature. Thus, if the loading machine is kept at low temperature, and the stenting rings are formed of nickel-titanium shape memory alloy, this will facilitate loading into the surrounding sheath of a delivery catheter, and reduce friction forces between the radially outward facing abluminal surface of the stent graft and the lumen of the sheath, and similarly reduce endwise stress within the spiral form ALFER insertion tool.

Once the stent graft has been advanced until its full length is within the confining sheath of the stent graft delivery system, the stent graft sub-assembly of surrounding sheath, graft, and spiral formed rod squeezed within the lumen of the stent graft, can be coupled up to the other components of the catheter delivery system, including structure of the proximal end of the system for maintaining the position of the spiral formed rod relative to the stenting site, while the surrounding confining sheath may be progressively withdrawn proximally, under control from the proximal end of the delivery system outside the body of the patient receiving the stent graft. As with any delivery system, there will of course be valves and ports for passing flushing liquid and disclosing liquids through the system.

It may be advantageous for the surrounding sheath to have a distal end tapered to a tip. For example, the tip technology disclosed in Applicant's WO 01/34061 is applicable to the present invention.

This disclosure is by way of embodiments presently preferred by the inventor. Being themselves persons skilled in the art, readers will be able to envisage and realise without inventive activity other embodiments within the scope of the claims which follow, and within the scope of the present disclosure.

What is claimed is:

1. A method of loading a covered self-expanding stent into a delivery sheath, comprising:

providing a covered self-expanding stent having a luminal covering layer and a length of 200 mm or more, the self-expanding stent comprising a collocation of stenting rings, each stenting ring spaced from an adjacent stenting ring, the stenting rings having an expanded configuration defining an expanded perimeter and a compressed configuration defining a compressed perimeter smaller than the expanded perimeter;

providing a stent pusher having an outer perimeter smaller than the compressed perimeter of the stenting rings, the stent pusher including protrusions arranged helically about a distal end of the stent pusher;

radially compressing the covered self-expanding stent over the protrusions, the protrusions pressing into the luminal covering layer;

disposing a delivery sheath over the covered self-expanding stent; and withdrawing the stent pusher by unscrewing it from the luminal covering layer.

2. The method according to claim 1, wherein the providing step includes helically winding a wire about an outer surface of a distal end of the stent pusher to form the protrusions.

3. The method according to claim 1, wherein the stent pusher comprises an inner catheter, further comprising the step of delivering the covered self-expanding stent to a stenting site, the inner catheter protrusions preventing proximal movement of the covered self-expanding stent upon removal of the delivery sheath.

4. The method according to claim 1, wherein the length of the covered self-expanding stent is approximately 500 mm, further comprising the step of delivering the covered self-expanding stent to a stenting site, the inner catheter protrusions preventing proximal movement of the covered self-expanding stent upon removal of the delivery sheath.

* * * * *